United States Patent [19]

Kawamura et al.

[11] Patent Number: 4,561,447
[45] Date of Patent: Dec. 31, 1985

[54] APPARATUS AND METHOD OF DETECTING ARTERIAL PULSE WAVE

[75] Inventors: Norio Kawamura, Nagoya; Hifumi Yokoe; Hideichi Tsuda, both of Kasugai, all of Japan

[73] Assignee: Nippon, Colin Co., Ltd., Japan

[21] Appl. No.: 569,501

[22] Filed: Jan. 9, 1984

[30] Foreign Application Priority Data

| Jan. 14, 1983 | [JP] | Japan | 58-4129[U] |
| Jan. 17, 1983 | [JP] | Japan | 58-5561 |
| Jan. 18, 1983 | [JP] | Japan | 58-5148[U] |
| Jan. 18, 1983 | [JP] | Japan | 58-5149[U] |
| Jan. 18, 1983 | [JP] | Japan | 58-6174 |

[51] Int. Cl.[4] ............................................. A61B 5/02
[52] U.S. Cl. .................................... 128/687; 128/706
[58] Field of Search ................ 128/687, 688, 689, 706

[56] References Cited

U.S. PATENT DOCUMENTS

| 2,702,883 | 2/1955 | Petroff et al. | 128/687 |
| 3,299,882 | 1/1967 | Masino | 128/687 |
| 3,811,429 | 5/1974 | Fletcher et al. | 128/687 |

Primary Examiner—D. E. Gantz
Assistant Examiner—A. Pal
Attorney, Agent, or Firm—Parkhurst & Oliff

[57] ABSTRACT

An apparatus for detecting and displaying a pulse wave based on pulsations of an arterial vessel of a human body, with an improved accuracy irrespective of variations in pressing force of a sensing unit against a body member and/or irrespective of deviation of the depressed sensing unit from the arterial vessel to be detected, thereby providing the user of the apparatus with reliable medical diagnostic information on blood circulating organs.

26 Claims, 22 Drawing Figures

* VARIABLE-SENSITIVITY AMPLIFIER

APPARATUS AND METHOD OF DETECTING ARTERIAL PULSE WAVE

BACKGROUND OF THE INVENTION

The present invention relates to technologies for accurate detection of a pulse wave based on pulsations of an arterial vessel below an epidermal tissue of a living being, such as the carotid and thigh arteries, and for faithful indication of the detected pulse wave.

It is known in the art that blood pressure pulsations (hereinafter referred to as "pulse wave") of arteries caused by heartbeats of a living being represent working conditions of the heart, and consequently the detection of the pulse wave provides important medical information on troubles or diseases of the heart or the arterial vessels. For this reason, it has been practiced to diagnose blood circulatory organs of a subject by utilizing an apparatus which is capable of detecting and displaying such a pulse wave.

To obtain the pulse wave, such apparatus as indicated above is applied, for example and usually, to the carotid artery, which is a thick arterial vessel located right below the epidermal tissue and comparatively close to the heart. A commonly used apparatus includes a sensing unit which comprises a housing, a presser member, and an elastic member which is equipped with a strain gauge. The sensing unit is depressed onto the neck of a subject (e.g., a human being) such that the presser member protruding from the housing is pressed against the carotid artery via the epidermal tissue, and the pulsations (contracting and expanding movements) of the carotid artery which are transmitted as a carotid artery pulse wave to the elastic member through the presser member, are detected as an elastic deformation of the elastic member, which is converted by the strain gauge into electrical signals.

However, in the conventionally proposed apparatus of the type described above for detection of a carotid artery pulse wave, the elastic member pushing the presser member is directly secured and supported by to the housing structure, and therefore a pressure of depression between the carotid artery and the presser member (hereinafter called simply "depression pressure") is extremely easily and sensitively affected by a pressing force exerted to the housing of the sensing unit upon depression thereof onto the neck. Thus, the traditional apparatus suffers considerable difficulty in achieving faithful and accurate detection of the carotid artery pulse wave. Stated in more detail, the hypodermal tissue existing between the presser member and the carotid artery tends to function as an elastic body, whereby if the depression pressure is too low, the pulsating movements of the carotid artery, i.e., pulse waves are absorbed by the hypodermal tissue and accordingly the pulsations are not sufficiently transmitted to the presser member of the sensing unit, resulting in distortion of the pulse wave detected. On the other hand, if the depression pressure is excessively high, the pulsating movements of the carotid artery are impeded, with a result of failing to obtain the pulse wave of the carotid artery while it is normally functioning. Hence, to sufficiently faithfully detect the pulse wave of the carotid artery in its normally functioning condition in the form of vibrations of the presser member, it is necessary to depress the carotid artery with a pressure neither too high nor too low, i.e., with a suitable pressure, that is, to press the housing of the sensing unit against the neck of the subject with a suitable force. However, it is very difficult to make sure that the carotid artery is depressed with a suitable pressure, and also difficult to maintain the pressing force at a proper level during detection of the pulse wave. This difficulty has been a cause for the problem of distortion of the detected pulse wave.

Further, the faithful and accurate indication of a pulse wave of the carotid artery by the apparatus as described above, requires its protruding presser member to be depressed onto an outermost layer of the neck skin within a comparatively limited elongate area along a length of the carotid artery close to the surface of the skin layer. This means a need for a user of the apparatus to exercise an utmost care and a relatively high level of skill in positioning the sensing unit on the neck upon depression of the presser member, so that the pulse wave of the carotid artery can be obtained with high accuracy and reliability. In other words, a positional deviation of the presser member from the limited elongate area of the neck skin will result in a corresponding degree of absorption of the pulsations of the carotid artery by the hypodermal tissue of the neck, and lead to a resultant distortion of the pulse wave to be detected by the detecting apparatus.

SUMMARY OF THE INVENTION

Accordingly, it is a first object of the invention which was developed in view of the above described situation, to provide an apparatus for detecting a blood pressure pulse wave of an arterial vessel of a living subject, with ease of manipulation and with high detecting reliability, irrespective of variations in pressing force applied to the housing of a sensing unit upon depression thereof onto an appropriate part of the subject.

A second object of the invention is the provision of such detecting apparatus having a sensing unit which can be kept depressed in place on the subject with an optimal range of stabilized pressure.

A third object of the invention is to provide a carotid artery pulse wave detecting device wherein a sensing unit can be readily positioned and depressed, without a special skill, in a comparatively narrow area of the neck through which the carotid artery runs and in which the pulse wave of the artery can be faithfully detected.

A further object of the invention is the provision of such detecting apparatus having a plurality of sensing units disposed on a depression surface of a detector housing, which is capable of detecting a pulse wave of an arterial vessel free of noises which are produced due to variations in the pressing force of the sensing unit onto the subject and which would be otherwise added to the detected result.

According to one aspect of the invention, there is provided a pulse wave detecting apparatus, including a detector adapted to be depressed at its depression surface onto a body member of a subject to detect a pulse wave of an artery, said detector comprising:

a housing having portions defining an air chamber which is open at one end thereof, the open end of said housing defining a plane of said depression surface;

a sensing unit received in said air chamber movably in a first direction parallel to a direction in which the detector is depressed onto the body member, said sensing unit including a presser portion protruding away from said depression surface, said sensing unit detecting the pulse wave of said artery transmitted through said presser portion, and generating a pulse wave signal; and elastic support means provided in said housing for resiliently supporting said sensing unit, upon depression of the detector onto the body member, with an elastic force thereof so as to establish a depression pressure between said presser portion and the body member in a specified optimal range.

In the detector of the detecting apparatus constructed as described above, the sensing unit is movable within the housing in a direction parallel to a direction of depression of the sensing unit onto the body member, and biased by the elastic support means with an optimal range of force in the direction of depression, whereby the depressing force of the presser member of the sensing unit against the body member is stably held in a suitable range regardless of variations in pressing force applied to the housing by a clinician or other users of the apparatus. Thus, the varying level of the pressing force will not significantly affect the pulse wave to be detected, and prevent the pulse wave signal from being distorted, thereby permitting a reliable and faithful detection of the pulse wave of the artery.

According to another aspect of the invention, there is provided a pulse wave detecting apparatus, including a detector adapted to be depressed at its depression surface onto a body member of a subject to detect a blood pressure pulse wave of the artery, said detector comprising:

a sensing device depressed onto the body member and detecting the pulse wave of said artery to generate a pulse wave signal; and holder means carrying at one end thereof said sensing device and gripping, with a predetermined pressure of depression, the body member of the subject between the other end thereof and said sensing device, thereby holding said sensing device in contact with said body member of the subject at a predetermined portion of the latter with a predetermined force of depression.

In the detector of the detecting apparatus described above, the sensing device can be kept depressed on a body member of a subject such as the neck, thigh and upper arm, with a suitable pressure of depression, by simply gripping the body member between both ends of the holder means, whereby a distortion-free pulse wave of the artery can be obtained with high stability.

In accordance with a further aspect of the invention, there is provided a carotid artery pulse wave detecting apparatus, including a detector adapted to be depressed at its depression surface onto the neck of a subject to detect a blood pressure pulse wave of the carotid artery, said detector comprising:

a housing having portions defining an air chamber which is open at one end thereof, the open end of said housing defining a plane of said depression surface; and a plurality of sensing units each received in said air chamber movably in a first direction parallel to a direction in which the detector is depressed onto the neck, each of said sensing units including a presser portion protruding away from said depression surface, said each sensing unit detecting the pulse wave of said carotid artery transmitted through said presser portion, and generating a pulse wave signal, the presser portions of said sensing units being disposed such that a plurality thereof are disposed along a line intersecting the carotid artery and spaced from each other by a distance of not more than 15 mm in a second direction perpendicular to said carotid artery, when the detector is depressed onto the neck of the subject.

In the detector of the above apparatus, the presser portion of one of the plural sensing units can be easily positioned within a comparatively narrow limited area of the neck in the vicinity of the carotid artery, thus requiring no special skill in detecting a distortion-free pulse wave of the carotid artery.

In accordance with a still further aspect of the invention, there is provided a method of detecting blood pressure pulsations of an artery of a subject and displaying a pulse wave form thereof, based on pulse wave signals generated from a plurality of sensing units disposed in a housing of a detector which is adapted to be depressed at its depression surface onto an appropriate part of said subject, said method comprising the steps of:

comparing amplitudes of said pulse wave signals with each other, and determining one of said pulse wave signals to be a maximum-amplitude pulse wave signal;

weighting said pulse wave signals by applying a positive weight to said maximum-amplitude pulse wave signal and negative weights to the other pulse wave signals, a sum of said positive weight and said negative weights being zero;

averaging the weighted pulse wave signals to produce an average pulse wave signal; and displaying said pulse wave form of said artery in response to said average pulse wave signal.

In the above described method, the pulse wave signals generated from the individual sensing units are weighted by applying a plus weight to the maximum-amplitude pulse wave and minus weights to the other pulse wave signals such that a sum of the one plus weight and the other minus weights is equal to zero. The weighted pulse wave signals are averaged into an average pulse wave signal upon which the pulsations of the artery is displayed, whereby noises which are possibly included in the individual pulse wave signals, due to variations in the pressing force of the housing against the body member and/or displacement of the sensing units relative to the subject, are effectively eliminated from the average pulse wave signal, thus allowing the actual pulsations of the artery to be accurately displayed.

An apparatus suitable for practicing the above detecting method, also provided according to the invention, comprises:

a detector including a housing an a plurality of sensing units which are received in said housing and adapted to be depressed onto a body member of a subject to detect a blood pressure pulse wave of an artery, said sensing units generating pulse wave signals representing pulsations of the artery;

variable amplifier means, connected to said sensing units, for amplifying said pulse wave signals from the respective sensing units;

averaging means for averaging said pulse wave signals amplified by said variable amplifier means, and producing an average pulse wave signal;

display means for displaying a pulse wave form representing the pulsations of the artery, based on said average pulse wave signal; and control means including means for determining one of said pulse wave signals from said sensing units to be a maximum-amplitude pulse wave signal, said control means directing said variable amplifier means to amplify said maximum-amplitude pulse wave signal by a positive amplification factor and the other pulse wave signals by negative amplification factors, a sum of said positive amplification factor and said negative amplification factors being zero.

In the detecting apparatus constructed as described above, the variable amplifier means amplifies the maximum-amplitude pulse wave signal by a plus factor of amplification, and the other pulse wave signals by minus factors of amplification, such the a sum of values of these plus and minus factors is equal to zero. The amplified pulse wave signals are averaged by the averaging means into an average pulse wave signal upon which the pulsations of the artery is indicated on the display means, whereby noises possibly included in the detected pulse wave signals are effectively eliminated from the average pulse wave signal.

BRIEF DESCRIPTION OF THE DRAWINGS

The above and other objects, features and advantages of the present invention will become more apparent from reading the following description of the preferred embodiments taken in connection with the accompanying drawings in which.

DESCRIPTION OF THE PREFERRED EMBODIMENTS

Figure 1:
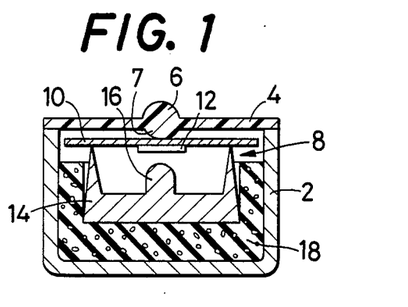
FIG. 1 is a cross sectional elevational view of one embodiment of a carotid artery pulse wave detecting apparatus according to present invention.
Figures 2, 3, 5:
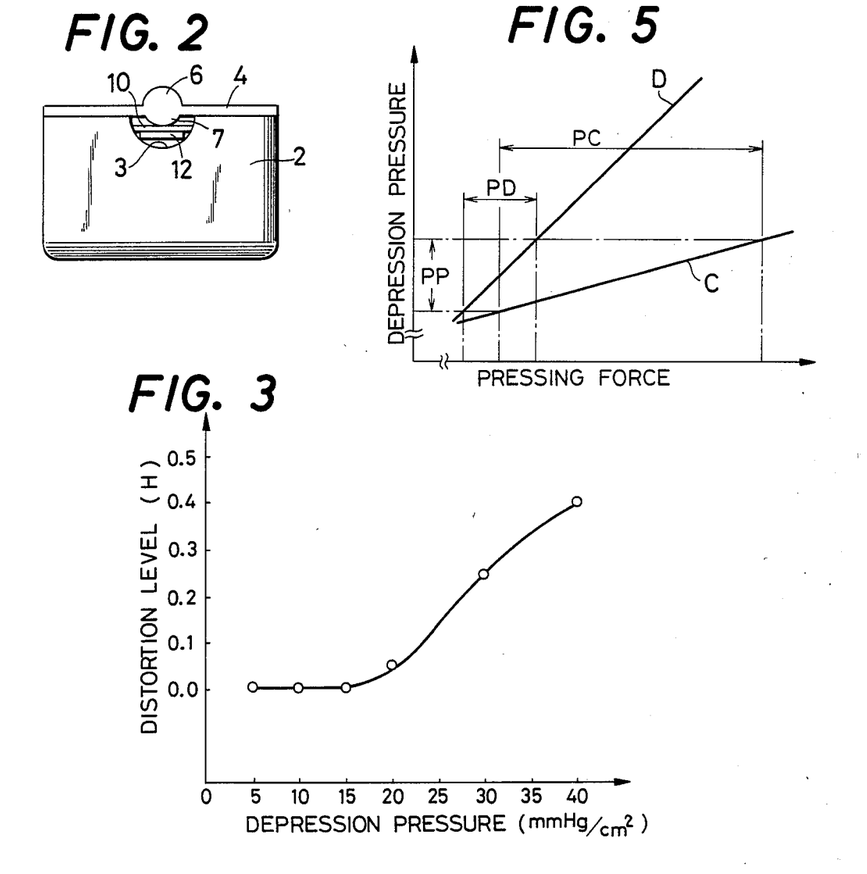
FIG. 2 is an elevational view of the detecting apparatus of FIG. 1.
FIG. 3 is a graphical representation illustrating an optimal range of depression pressure of a presser member of the apparatus against the skin layer of the neck of a subject.
FIG. 5 is a graph showing a depression pressure of the presser member against the skin layer in relation to a pressing force applied to a housing of the apparatus of FIGS. 1 and 2, and to a housing of a known apparatus.

Referring to the accompanying drawings which show preferred embodiments of the invention, there is shown in FIG. 1 one form of a detector including a sensing unit which comprises a box-like housing 2. This housing 2 is a rigid structure of metal, platics or other materials having an air chamber which is open at one end thereof. The open end of the housing 2 defines a plane of a depression surface of the detector at which the detector is forced against the neck of a subject, e.g., a human body. The opposite walls on the long sides of the box structure of the housing 2, have opposite recesses 3 in the middle parts thereof and at the open end of the housing structure, as shown in FIG. 2. A resilient diaphragm 4 is bonded, at its opposite ends, to the open ends of the other pair of opposite walls on the short sides of the housing structure. This resilient diaphragm 4, which covers or closes the air chamber and forms the depression surface of the detector, is made of plastic, rubber or other elastic materials and includes a central movable portion. The movable portion of the diaphragm 4 comprises an integrally formed presser portion 6 which protrudes away from the air chamber of the housing 2, i.e., away from the depression surface in the direction in which the detector (housing 2) is depressed onto a body member such as the neck for detection of a pulse wave of the carotid artery. On the other side of the central movable portion opposite to the presser portion 6, there is integrally formed an abutment portion 7 which protrudes toward the inside of the housing 2. Stated more specifically, the presser portion 6 and the abutment portion 7 are supported by the central movable portion of the resilient diaphragm 4 such that the two portions 6, 7 are movable in a direction perpendicular to the depression surface of the detector which lies in the plane including the open end of the housing 2. When the detector is pressed onto the neck of the human body at the open end of the housing 2, the presser portion 6 is depressed onto a skin layer near the carotid artery with a given pressure of depression between the presser portion 6 and the skin layer, and moved in the direction parallel to the depressing direction in response to blood pressure pulsations of the carotid artery.

Within the air chamber of the housing 2 is disposed a sensing unit 8 to detect an amount of movements of the presser portion 6, that is, to detect pulsating movements of the carotid artery. The sensing unit 8 comprises the resilient diaphragm 4 having the presser portion 6 described above, an elastic member 10 made of a spring sheet material, a semiconductor or other type of strain gauge 12 secured with an adhesive to a central portion of the elastic member 10, and a support structure 14. The elastic member 10 is an elastically deformable planar member which is supported at its opposite ends by supporting arms of the support structure 14 which is made of metal, plastics or other rigid materials. The elastic member 10 is thus deformable at its central portion in the direction across the thickness thereof, so that the central portion contacting the presser portion 6 via the abutment portion 7 is flexed according to the movements of the presser portion 6. The strain gauge 12 adheres to the rear surface of the elastic member 10 in an area opposite to a portion of the central front surface thereof engaging the abutment portion 7, and converts varying amounts of flexure or elastic deformation of the central portion of the elastic member 10, into variations in electrical resistance and thus into electrical signals representing a blood pressure pulse wave of the carotid artery (hereinafter referred to as "pulse wave signal"). The pulse wave signal generated by the strain gauge 12 is fed to a pulse wave signal output device (not shown) through leads wires (not shown).

Thus, the sensing unit 8 serves to provide an electrical pulse wave signal representing a pulse wave of the carotid artery which reflects an amount of movement of the presser portion 6, that is, a variation in blood pressure in the carotid artery. The blood pressure pulse wave is displayed in response to the thus obtained pulse wave signal. Reference numeral 16 designates a stop 16 which extends from the central portion of the support structure 14 for protecting the strain gauge 12 from being damaged due to an excessive flexure or deflection of the elastic member 10.

The housing 2 further houses an elastic support member 18 made of a sponge or other compressible or yieldable material. This elastic support member 18 which functions as elastic support means, is fitted in the air chamber of the housing 2 and bonded to the inner surfaces of the housing. The support member 18 defines an internal opening accommodating the rigid support structure 14 which is bonded to the member 18. Thus, the sensing unit 8 including the rigid support structure 14 is movable in the direction toward the bottom of the housing (in the direction opposite to the depressing direction) through yielding of the elastic support member 18.

When a pulse wave of the carotid artery is detected by the apparatus equipped with the detector constructed as discussed hereinbefore, the user of the apparatus depresses the detector onto the neck in such manner that the length or long side walls of the housing 2 is orthogonal to the carotid artery and such that the recesses 3 in the long side walls of the housing 2 are located above the line of extension of the carotid artery. The amount of protrusion of the presser portion 6 away from the housing 2 (away from the plane of the depression surface), the modulus of elasticity of the elastic support member 18, and other parameters are selected so that the pressure of depression between the detector (depression surface thereof) and the neck of the subject is held in an optimal range, irrespective of a specific pressing force exerted to the housing 2 (detector) by the user. More particularly, those parameters are determined so that the depression pressure is not less than about 5 mmHg/cm² even when the housing 2 is pressed with the depression surface held in slight contact with the skin of the neck, and not more than about 15 mmHg/cm² even when the housing 2 is pressed against the neck with a considerably large force.

With the depression pressure of the presser portion 6 against to the neck skin determined as described above, the mere depression of the detector for contact of the depression surface with the neck skin will suffice to assure easy establishment of a depression pressure between the presser portion 6 and the neck within the specified optimum range. In other words, the depression pressure can be stably maintained at a permissible level even when the pressing force being applied to the housing 2 is unintentionally increased due to oscillatory movements of the user's hand holding the housing 2.

Figure 4:
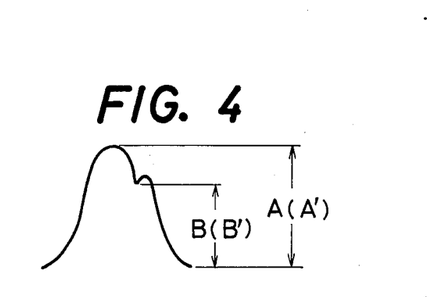
FIG. 4 is a diagrammatic view showing an amplitude of a pulse wave signal and a level of a notch of the pulse wave signal.

Described in further detail, the present inventors found through their research and experiments that the optimal range of depression pressure is between 5 and 15 mmHg/cm². The maintenance of the depression pressure in the above range is preferred for accurate or exact detection of the pulse wave of the carotid artery. FIG. 3 graphically shows a result of experiments upon which the present inventors arrived at the recognition that the range of pressure specified above is considered optimum. The graph in FIG. 3 represents a level of distortion H of the detected pulse wave signal, varying with a depression pressure applied to an area of the neck skin in the vicinity of the carotid artery. This graphical representation clearly indicates that the distortion level H is satisfactorily low in the range of depression pressure from approx. 5 mmHg/cm² up to approx. 15 mmHg/cm². In this connection, it is noted that the distortion level H is expressed by the following equation:

$$H = \frac{B'/A' - B/A}{B/A}$$

where, as illustrated in FIG. 4, A and B represent an amplitude of a nominal or standard distortion-free pulse wave signal and a level of a notch of the pulse waveform (V-shaped notch resulting from closure of the aortic valve), respectively, and A' and B' represent an amplitude of an actually detected pulse wave signal and a level of its notch when thepulse wave is distored due to excessive depression pressure against the carotid artery.

When the depression pressure between the presser portion 6 and the neck skin is determined to fall within the range specified above, the depression pressure varies in relation to a pressing force applied to the housing 2, as shown in the graph of FIG. 5. Solid line C shows the pressure-force relation of the instant apparatus, and solid line D shows that of a known apparatus. These lines show that the range PC of pressing force of the instant apparatus corresponding to the specified range of depression pressure (5-15 mmHg/cm²) is extremely wider than the corresponding range PD of the known apparatus.

While there have been described the general parameter conditions including the amount of protrusion of the presser portion 6 from the depression surface of the detector, and the elastic modulus of the elastic support member 18, it is needless to say, from the standpoint of maintaining an optimal depression pressure under any magnitude of a pressing force of the housing 2, that the elastic modulus of the elastic support member 18 is desired to be kept at a level as low as practicable to such extent as to prevent excessive absorption of oscillatory movements of the presser portion 6 responsive to the pulsations of the carotid artery, i.e., as to enable the strain gauge 12 to provide a sufficiently faithful pulse wave signal. In this embodiment, the elastic modulus of the elastic support member 18 is so selected as to meet the above requirement. An excessively low modulus of elasticity of the elastic support member 18 will result in failure to provide a sufficient pressure of depression, causing the pulse wave signal obtained by the sensing unit 8 to be very low in level and consequently distorted. In the case where the modulus of elasticity is set excessively high, the range of pressing force corresponding to the specified optimal range of depression pressure is very narrow, and therefore the depression pressure becomes too high, causing the pulse wave signal to be distorted.

As is apparent from the foregoing description of the present embodiment of the detecting apparatus, a pulse wave signal which is faithfully and accurately responsive to a pulse wave of the carotid artery may be obtained by simply holding the depression surface of the detector in close contact with the appropriate portion of the neck.

Further, as previously indicated, the detector is positioned relative to the carotid artery such that the opposite recesses 3 in the housing 2 are aligned with the line of extension of the carotid artery. Therefore, the recesses 3 provides an advantage of serving as means for protecting the carotid artery against excessive depression by the open end edges of the long side walls of the housing 2 when the detector is depressed onto the neck, thereby preventing otherwise possible distortion of the pulse wave signal.

The previously stated conditions for establishing the optimal range of depression pressure of the presser portion 6 against the neck are considered to be met with a satisfactory result if the modulus of elasticity of the elastic support member 18 is not excessively low and if a permissible level of depression pressure of the presser portion 6 is obtained as long as the pressing force of the housing 2 exerted to the neck is held within a normal range, neither too small nor too large.

The elastic support member 1 may be a coil or sheet spring or springs, or other elastic or resilient members which permit the sensing unit 8 to be retracted toward the bottom of the housing 2, that is, away from the neck skin.

Similarly, the sensing unit 8 may be provided in other suitable forms; it may be replaced, for example, by a pressure-sensitive detector wherein the movements of the presser portion 6 are converted into a pressure variation of a liquid to be detected.

While the presser portion 6 is formed as an integral part of the resilient diaphragm 4, the former may be formed separately from the latter and joined to each other as a unitary member. The abutment portion 7 which is designed to directly engage the elastic member 10 in the present embodiment, may be adapted to indirectly engage the elastic member 10 through an intermediate member.

Although the instant detector is of rectangular configuration, it may be a cylindrical structure which, for example, is formed by rotating the cross section of FIG. 1 about the vertical axis and which has a cross section identical to that of FIG. 1.

While the above detector is depressed onto the neck to detect a pulse wave of the carotid artery, it may be used in depression onto a thigh or an eyeball of a human subject to detect a pulse wave based on pulsations of a thigh artery or of an artery near the eyeball.

Referring next to FIGS. 6-9, there is described another embodiment of the detecting apparatus having a detector which includes a plurality of sensing units.

Figure 6:
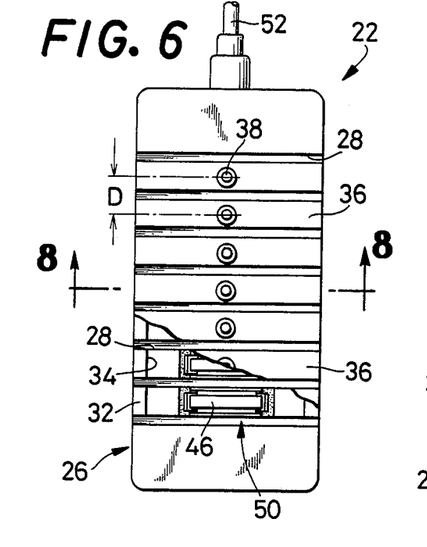
FIG. 6 is a front elevational view partly in cross section of another embodiment of the detecting apparatus of the invention.
Figure 7:
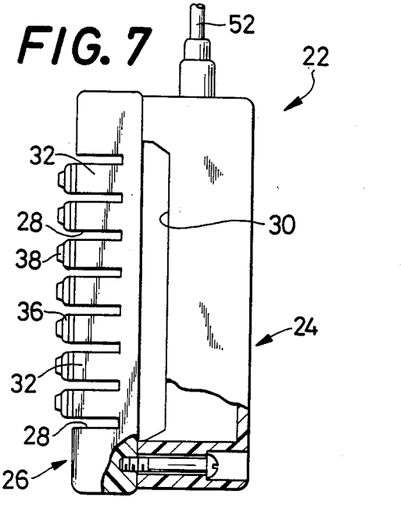
FIG. 7 is a side elevational view partly in cross section of the apparatus of FIG. 6.
Figure 8:
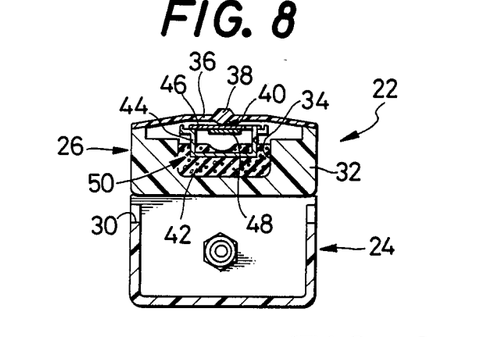
FIG. 8 is a cross sectional view taken along line 8—8 of FIG. 6.

In FIGS. 6-8, reference numeral 22 indicates a detector of a detecting apparatus for detecting a pulse wave of an artery such as the carotid or thigh artery. The detector 22 includes a support block 24 and a housing 26. The support block 24 is of rectangular box-like structure. The housing 26 is fixed at its longitudinal ends to the support block 24 such that the bottom of the housing 26 closes an opening of the support block 24.

The housing 26 is made of an elastic synthetic resin material and has a plurality of slots 28 which are open on the side opposite to the side facing the support block 24, i.e., open in the depression surface of the detector 22. The slots 28 are formed in parallel to each other along the width of the housing 26, and spaced from each other along the length of the housing 26 by a predetermined distance D, e.g., 8 mm. Thus, the housing 26 has plural thin portions corresponding to the longitudinally spaced slots 28. The opposite walls along the length of the support block 24 have recesses 30 in their open end portions between their longitudinal ends. This arrangement of the support block 24 allows the housing 26 to be flexed or deflected as a whole toward and away from the bottom of the support block 24.

The spaced-apart slots 28 of the housing 26 define a plurality of rectangular holder portions 32 which accommodate respective sensing units. Each of the holder portions 32 has a stepped groove 34 in a central portion thereof in the width direction, as shown in FIG. 8. A resilient diaphragm 36 is bonded to the longitudinal ends of the holder portion 32 so that the diaphragm 36 spans and closes the stepped groove 34. The resilient diaphragm 36 which is made of an elastic synthetic resin material, has an integrally formed presser portion 38 in its central portion, which protrudes from the outer surface of the diaphragm for depressing the neck of a human body. On the opposite side of the presser portion 38 is formed an abutment portion 40.

An elastic support member 42 of sponge rubber designed as elastic support means is bonded to a portion of the holder portion 32 defining the bottom of the stepped groove 34. A generally U-shaped rigid support structure 44 is partly embedded in the elastic support member 42. The ends of a pair of opposed arms of the rigid support member 44 support a planar metallic elastic member 46 in such manner as to allow the elastic member 46 to be elastically deformable but restrict its movement in a plane parallel to the depression surface of the detector 22. The abutment portion 40 is adapted to be in abutment on the central portion of the elastic member 46 while the presser portion 40 on the resilient diaphragm 36 is not in pressed contact with the neck of the subject. Upon depression of the presser portion 38 onto the neck, pulsating movements of the carotid artery are transmitted to the resilient diaphragm 36 via the hypodermal tissue of the neck, and then transmitted to the elastic member 46 via the abutment portion 40.

A strain gauge 48 is bonded to a rear surface of the metallic elastic member 46 opposite to the front surface on which the abutment portion 40 abuts. The strain gauge is adapted to generate electric signals corresponding to a flexure or deflection of the elastic member 46. Stated the other way, the oscillatory movements transmitted to the elastic member 46 via the abutment portion 40 are electrically detected. Thus, in the detector 22 of the this embodiment, the resilient diaphragm 36 having the presser member 38, the rigid support 44, the metallic elastic member 46 and the strain gauge 48 constitute a sensing unit 50 for electrical detection of the movements of the abutment portion 40 (presser portion 38). This sensing unit 50 is provided in each of the holder portions 32. The strain gauges 48 of the invdividual sensing units 50 are connected to an external signal processing circuit with respective lead wires (not shown) in the form of a multicore cable fixed at one end thereof to the support block 24, and the pulse wave signals from the strain gauges 48 are processed by the processing circuit and indicated on a display device (not shown). As previously described in connection with the first embodiment, the amount of protrusion of the presser portion 38 and the elastic modulus of the elastic support member 42 are selected so that the depression pressure between the presser portion 38 and the neck of the human body is held within a specified optimal range, e.g., between 5 and 15 mmHg/cm$^2$, irrespective of variations in pressing force applied to the housing 26.

When a pulse wave of the carotid artery is detected by the detector 22 constructed as described above, the detector 22 is held at its holder block 24 and depressed at its depression surface onto the neck of the subject.

In depressing the detector 22, it is desired to position the detector 22 such that the length of the housing 26 intersects, preferably at a right angle, the line of extension of a portion of the carotid artery close to the surface of the neck skin. By so positioning the detector 22 upon depression thereof onto the neck, the plural presser portions 38 are spaced along a line intersecting the carotid artery, thereby allowing one of the plural presser portions 38 to be located within an area of the neck skin in which the pulse wave of the carotid artery can be detected as a sufficiently high level of electric signals without a distortion, that is, detected with extreme accuracy and reliability.

Figure 9:
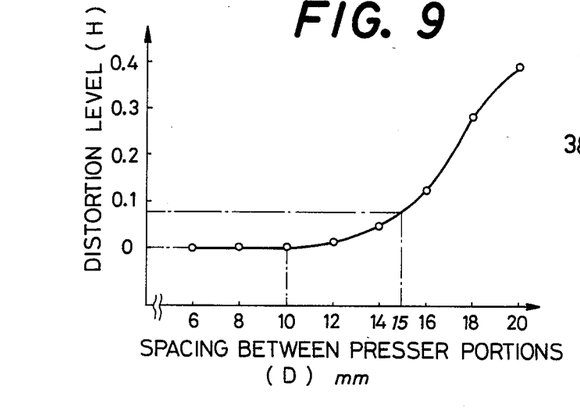
FIG. 9 is a graphical representation of a distortion level (H) of a detected pulse wave signal in relation to a spacing between adjacent presser members of the apparatus of FIGS. 6-8.

The above advantage of the detector 22 is evident from the graph of FIG. 9 depicting a relation between a spacing of the presser portions 38 and a distortion level of the obtained pulse wave signal, which relation was found based on experiments by the present inventors. This graph reveals that the distortion level of the pulse wave signal is at a very low level when the spacing D of the presser portions 38 is not more than 15 mm, and substantially equal to zero when the spacing is not more than 10 mm.

Another advantage of the detector 22 of this embodiment accrues from its arrangement wherein the housing 26 is adapted to be flexed or deflected in the direction normal to the depression surface of the detector. That is, all of the presser portions 38 may snugly fit the profile of the neck with almost equal pressure of depression when the detector 22 is pressed against the neck so as to cross the carotid artery. Consequently, the detection of the pulse wave of the carotid artery can be accomplished by any of the presser portions 38 with a comparatively high stability.

Figure 10:
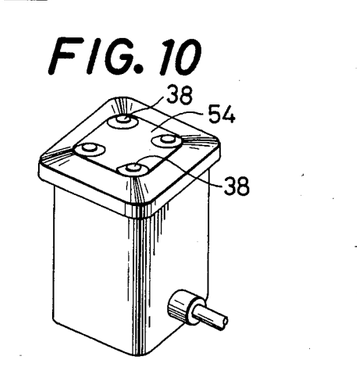
FIGS. 10 and 11 are perspective views of modified forms of a detector alternative to the detector of FIGS. 6-8.
Figure 11:
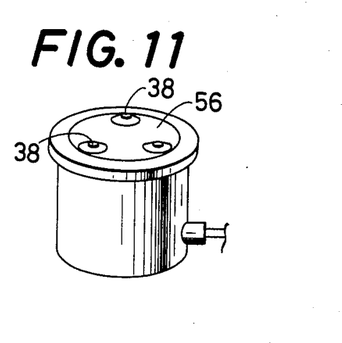

Although the presser portions 38 of the detector 22 are spaced along a straight line along the length of the housing 26, such linear arrangement is not a prerequisite. It is appreciated, for example, to arrange the presser portions 38 on a single common resilient diaphragm 54 or 56 as shown in FIGS. 10 and 11, respectively. At any rate, however, the individual presser portions 38 should be spaced from each other by a distance of not more than 15 mm in a direction perpendicular to the carotid artery when the detector is depressed onto the neck. When the presser portions or members 38 are disposed on a common resilient member like the diaphragm 54, 56 of FIGS. 10, 11, a sensing unit including the plural presser portions 38 may be directly attached to a housing, but it is preferred to use elastic support means (like the elastic support member 42) for yieldingly or resiliently supporting the sensing unit with respect to the housing.

There will be described another embodiment of a detecting apparatus of the invention wherein a sensing device is kept depressed on the neck of the subject without a need of holding the unit by a user (clinician or nurse) of the apparatus.

Figures 12, 13, 17, 18:
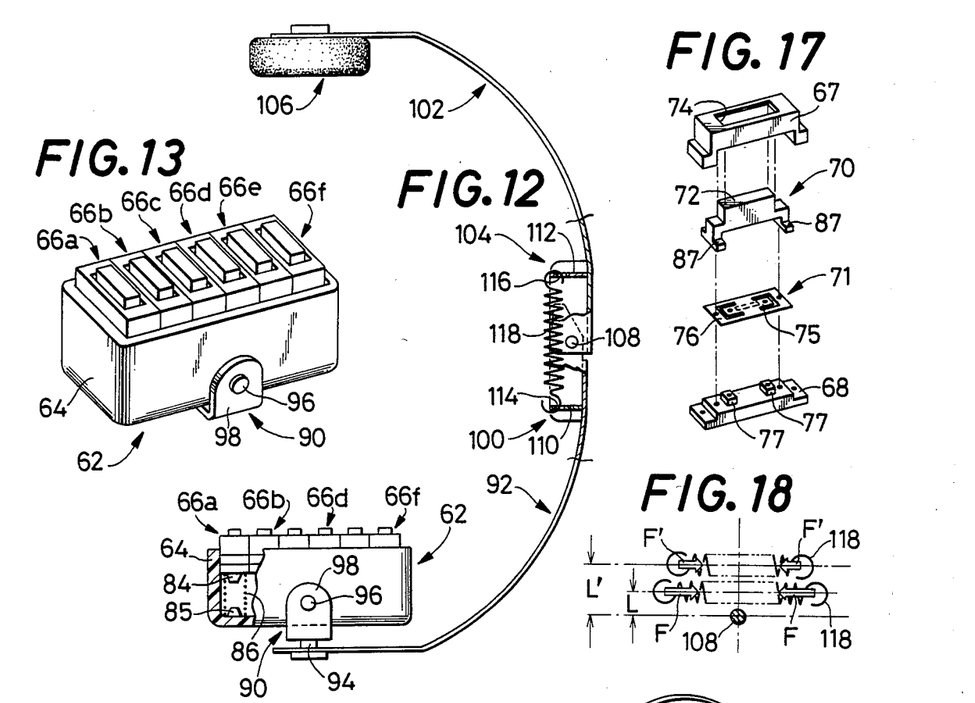
FIG. 12 is an elevational view partly in cross section of a detector of a further embodiment of the apparatus according to the invention.
FIG. 13 is a perspective view of a sensing device of the detector of FIG. 12.
FIG. 17 is an exploded view of the sensing unit of FIGS. 14-16 with its screws and other fasteners removed.
FIG. 18 is a diagrammatic view showing a pressing force of the sensing unit of FIG. 12, in relation to a change in size and configuration of a subject body to which the detector is applied.
Figure 14:
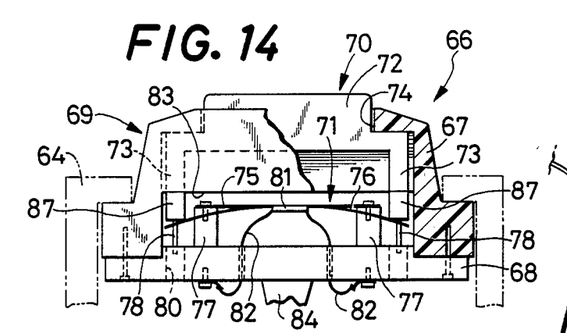
FIGS. 14, 15 and 16 are respectively, a partly cut-away view in front elevation of a sensing unit of the sensing device of FIG. 13, a plan view of the same with its upper housing and presser member removed, and a partly cut-away view in side elevation of the same sensing unit.
Figure 15:
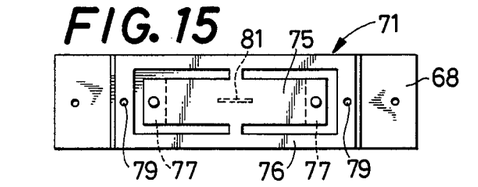

Referring first to a partly cut-away elevational view of FIG. 12 showing a detector of the apparatus, there is generally indicated at 62 a sensing device which includes a rectangular box-like housing 64 accommodating a plurality of sensing units 66 (six identical sensing units 66a–66f). As most clearly illustrated in FIG. 13, these sensing units 66a–66f are arranged along a line parallel to the length of the housing 64 with a predetermined spacing, 8 mm for example, from each other, and adapted to be movable in a direction parallel to the direction in which the sensing device 62 is depressed. Each of the sensing units 66 is capable of detecting a pulse wave of the carotid artery and produces an electrical pulse wave signal. This arrangement of the plural sensing units 66 in the longitudinal direction of the housing 64 as in the preceding embodiment allows detection of a pulse wave signal without a distortion which could be caused by misalignment of a detector or sensing device relative to the carotid artery when the detector has a single sensing unit.

Referring next to FIGS. 14–17 showning an example of the sensing unit 66 (FIG. 17 being an exploded view with all fasteners removed), numerals 67 and 68 indicate upper and lower housings which are assembled into an integral movable housing 69 accommodating a presser member 70 and a sheet spring 71. The presser member 70 has at its upper part a presser portion 72 to be depressed onto the neck, and a pair of leg portions 73 extending from the lower surface of the presser portion 72 at its longitudinal opposite ends. The presser portion 72 extends through an opening 74 defined by the upper part of the movable housing 69, and the presser member 70 is received movably in a vertical direction parallel to the direction of depression of the sensing unit 66. The sheet spring 71 includes an inner rectangular, relatively rigid sensed portion 75, and an outer rectangular, frame-like operated portion 76 which is relatively elastic, or more easily deformable than the sensed portion 75. The sensed portion 75 and the operated portion 76 are integrally united with each other at a longitudinal middle portion of the sheet spring 71. A pair of rectangular extensions 77 are provided extending from the upper surface of the lower housing 68, such that they are spaced a given distance from each other longitudinally of the lower housing. The sheet spring 71 is fixed, at the longitudinal opposite ends of its sensed portion 75, to the rectangular extensions 77, so that the longitudinal opposite ends of the operated portion 76 are held in abutment on the lower ends of the leg portions 73 of the presser member 70. In other words, the presser member 70 is biased by the sheet spring 71 in a direction away from the lower housing 68. A pair of columnar extensions 78 are provided extending from the lower ends of the leg portions 73 of the presser member 70, so as to be inserted through holes 79 formed in the opposite ends of the operated portion 76 of the sheet spring 71, whereby the presser member 70 is prevented from being laterally displaced relative to the sheet spring 71. The lower housing 68 has holes 80 in alignment with the columnar extensions 78, so that the extensions 78 are received in the holes 80 when the presser member 70 is moved toward the lower housing 68, thereby protecting the columnar extensions 78 with the lower housing 68. When the presser portion 72 of the presser member 70 is depressed against the neck of a living body, the presser member 70 is moved vertically relative to the movable housing 69 through pulsating movements of the carotid artery, and the vertical displacements of the presser member 70 are transmitted to the sensed portion 75 of the sheet spring 71 through the leg portions 73 and the operated portion 76 of the spring. Thus, the operated portion 76 is operated by the movements of the presser member 70 responsive to the arterial pulsations, and the sensed portion 75 has a strain based on the operated amounts of the operated portion 76.

A semi-conductor strain gauge 81 is bonded to a lower central surface of the sensed portion 75 of the sheet spring 71, to detect a strain or deformation of the sensed portion 75 and produce an electric signal corresponding to the detected strain. The signal from the strain gauge 81 is fed through lead wires 82 to a detection circuit (not shown) wherein a pulse wave signal is obtained based on an amount of displacement of the neck skin corresponding to the carotid artery pulsation.

As illustrated in FIG. 12, a projection 84 is formed on the lower surface of each sensing unit 66, and another projection 85 is formed on the bottom of the housing 64. These two projections 84 and 85 are opposed to each other, so that they locate and hold a compression coil spring 86 interposed as elastic support means between the sensing unit 66 and the housing 64. Thus, the sensing unit 66 is biased in a direction away from the lower projection 85. The coil spring 86 permits the sensing unit to be pressed into the housing 64 upon depression of the sensing device 62 onto the neck, thigh or upper arm. With this arrangement, a depression pressure between the presser member 70 and the neck can be held within an optimal range, e.g., 5–15 mmHg/cm$^2$, and consequently otherwise possible distortion of a detected pulse wave is prevented, even when the pressing force exerted to the housing 64 is varied in a considerable degree. The biasing force of the coil spring 86 is selected so as to maintain the depression pressure in the specified optimal range.

As discussed above, the displacements of the presser member 70 following the pulsating movements of the epidermal tissue of the neck are detected, as a pulse wave of the carotid artery, by the semi-conductor strain gauge 81. In this connection, it is noted that a comparatively large magnitude of displacement of the presser member 70 is converted into a small degree of strain of the strain gauge 81. Accordingly, the strain gauge 81 is protected against damage due to its excessive strain, and can be small in size and easily disposed without a positional or spatial limitation with respect to the other members of the sensing unit.

Figure 16:
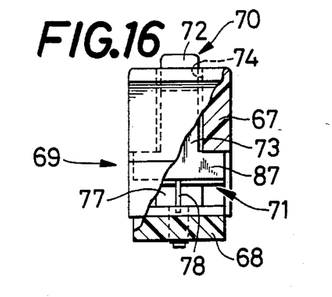

As illustrated in FIGS. 16 and 17, the leg portions 73 of the presser member 70 are formed with respective lateral tabs 87 which extend sideways into openings 83 formed through the side walls of the movable housing 69. These lateral tabs 87 cooperate with the housing walls defining the openings 83 to provide means for limiting the range of movement of the presser member 70, thereby preventing an excessive strain of the sensed portion 75.

The semi-conductor strain gauge 81 has a sensitivity so high as to sense a slight amount of strain of the sensed portion 75 which is provided as an elastic member similar to the member 10 of FIG. 1. Thus, the strain gauge 81 has a higher sensitivity than a traditional strain gauge.

The sensing device 62 having the plural sensing units 66 each constructed as discussed above, is carried by holder means which comprises a universal joint 90 and a generally arcuate first arm 92, as shown in FIG. 12. The universal joint 90 consists of: a first pivot pin 94 connected to one end of the first arcuate arm 92 and extending inwardly of the circular arc defined by the arm 92; a second pivot pin 96 connected to the housing 64 and extending in the width direction of the housing; and a link 98 which couples these two pivot pins 94 and 96 in perpendicular relation with each other, so that the sensing device 62 is pivotable about the second pivot pin 96 and the first arcuate arm is pivotable about the first pivot pin 94.

The other end of the first arm 92 opposite to said one end to which the sensing device 62 is pivotably connected, is formed into a first connector 100 by folding predetermined length of opposite lateral edge portions of the arm 92 inwardly of the circular arc, such that the first connector 100 is generally U-shaped in cross section.

The holder means further comprises a generally arcuate second arm 102 one end of which is formed into a second connector 104 of the same construction as the first connector 100. The other end of the second arm 102 carries a presser pad 106. The first and second arms 92 and 102 are pivotably connected to each other by a connecting pivot pin 108 which penetrates the first and second connectors 100 and 104 superposed at their ends one on the other, so that the connected two arms 92 and 102 are in a substantially semi-circular shape, as illustrated in FIG. 12, when the detector 22 is in service, i.e., placed on the subject. In this posture of the detector 22, the sensing device 66 are located in opposed relation with the presser pad 106. The first and second connectors 100 and 104 have respective end walls 110 and 112 which are opposed to each other with the connecting pivot pin 108 located therebetween. The end walls 110 and 112 are provided at their ends with respective engagement portions 114 and 116 to which the opposite ends of a tension coil spring 118 are attached. This tension spring 118 is positioned inside the connecting pivot pin 118 radially of the semi-circular arc defined by the arcuate arms 92, 102. With this arrangement, the tension coil spring 118 serves as tensioning means for biasing the first and second arcuate arms 92, 102 toward each other pivotably about the connecting pivot pin 108.

As described above, the detector is adapted to be attached to the neck of the subject with the sensing device 62 and the presser pad 106 gripping the neck therebetween with a tensile force of the coil spring 118. Thus, the first and second arcuate arms 92, 102, the presser pad 106 and the tension coil spring 118 constitute means for depressing the sensing deivce 62 of the instant detector of FIG. 12. This holder means enables the sensing device 62 to be kept pressed against the neck to depress the carotid artery with the resilient force of the tension coil spring 118, thereby preventing the sensing units 66 from picking up noises due to unstable holding of the sensing device by the user, and consequently permitting each sensing unit 66 to provide an output of noise-free pulse wave signal representative of actual blood pressure pulsations of the carotid artery.

The relation between the connecting pivot pin 108 and the engagement portions 114, 116 holding the coil spring 118, the relation of these elements to the arcuate arms 92, 102, the shapes and lengths of the arms 92, 102, etc. are determined, in order that a moment of force to be applied to the arcuate arms 92, 102 by the coil spring 118 is kept at a substantially constant level as long as the distance between the sensing device 62 and the presser pad 106 in service is held within a range of variation corresponding to a normally expected difference in size of the neck between the subjects. Therefore, the pressing force of the sensing device 62 against the neck is held substantially constant irrespective of the specific neck size of the subject.

Described in more detail with reference to FIG. 18 whrein L and L' represent a perpendicular distance from the axis of the connecting pivot pin 108 to the tension coil spring 118, and F and F' represent a tensile force of the coil spring 118 exerted to the arcuate arms 92 and 102, a product L×F or L'×F' (moment of force) is held substantially constant under normally expected operating conditions of the detector, i.e., irrespective of changes in angle formed by the two arcuate arms 92 and 102 and in length of the coil spring 118.

With the above indicated moment of force set at a suitable value, the pressure of depression between the presser member 70 of each sensing unit 66 and the neck of the subject can be kept in the specified optimal range, and thus the sensing unit 66 is adapted to be immune to a difference in neck size between the subjects, and able to detect blood pressure pulsations of the carotid artery in the form of a distortion-free pulse wave signal of sufficient amplitude.

As is apparent from the foregoing description, the instant detector is assured of distortion- and noise-free pulse wave signal faithfully indicative of the carotid artery pulsations, by a simple setting of the detector on the subject so as to grip the neck between the sensing device 62 and the presser pad 16 with the sensing device 62 positioned at an area of the neck skin under which the carotid artery is supposed to run.

The instant detector is also advantageous for its high adaptability to difference in configuration of the neck between the subjects, as well as to the difference in the neck size.

Although this embodiment employs the presser pad 106, it is not an element essential to the detector according to the principle of the invention. That is, the end of the second arcuate arm 102 remote from the connector 104 may be pressed in direct contact with the neck.

Similarly, the universal joint 90 may be eliminated; the sensing device 62 may be directly attached to the first arcuate arm 92. It is appreciated to adapt each sensing unit 66 to be pivotable (rotatable) in the housing 64 in a plane parallel to its width and perpendicular to its bottom so that the presser members 70 of the sensing device 62 may fit the neck more snugly while following its contour.

While the sensing device 62 has been described with a certain degree of particularity, various changes may be made in connection with this embodient of FIGS. 12-18 which are provided only for illustrative purpose and should not be construe to limit the invention. For example, the sensing units 66 which are resiliently supported by the springs 86 may be directly secured to the housing 64. Further, the number of the sensing units 66 (66a-66f) may be changed as needed. It is also possible to modify the overall construction or configuration of the sensing device 62 depending upon obvious modifications of the sensing units 66 in shape, arrangement, number, etc.

Figure 19:
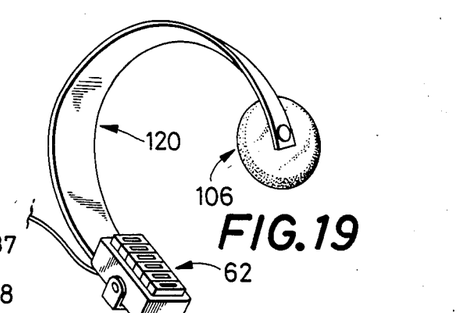
FIG. 19 is a perspective view of a modified form of a detector alternative to the detector of FIG. 12.

Furthermore, the holder means for the sensing device 62 may be modified as desired. For example, the holder means including the two arms 92, 102 may be replaced by a single resilient semi-circular arm 120 with a presser pad 106 fixed at one end thereof, as shown in FIG. 19. In this instance, the sensing device is depressed against the neck with a resilient force of the arm 120 rather than with a biasing force of a separate biasing member like the coil spring 118 used in the preceding embodiment.

Figure 20:
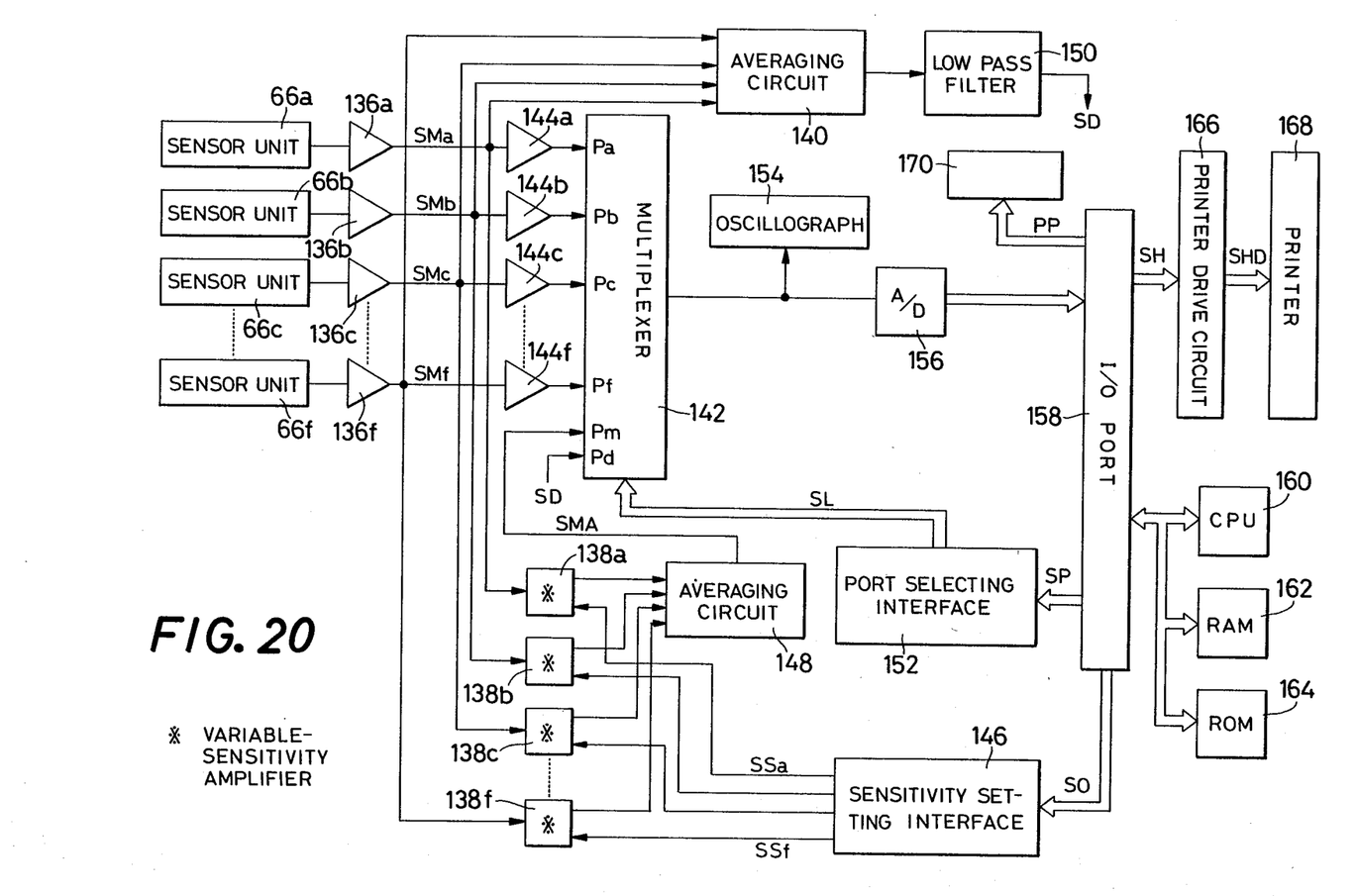
FIG. 20 is a schematic block diagram showing an embodiment of a control circuit of an apparatus using the detecor of FIGS. 12-17.
Figure 21:
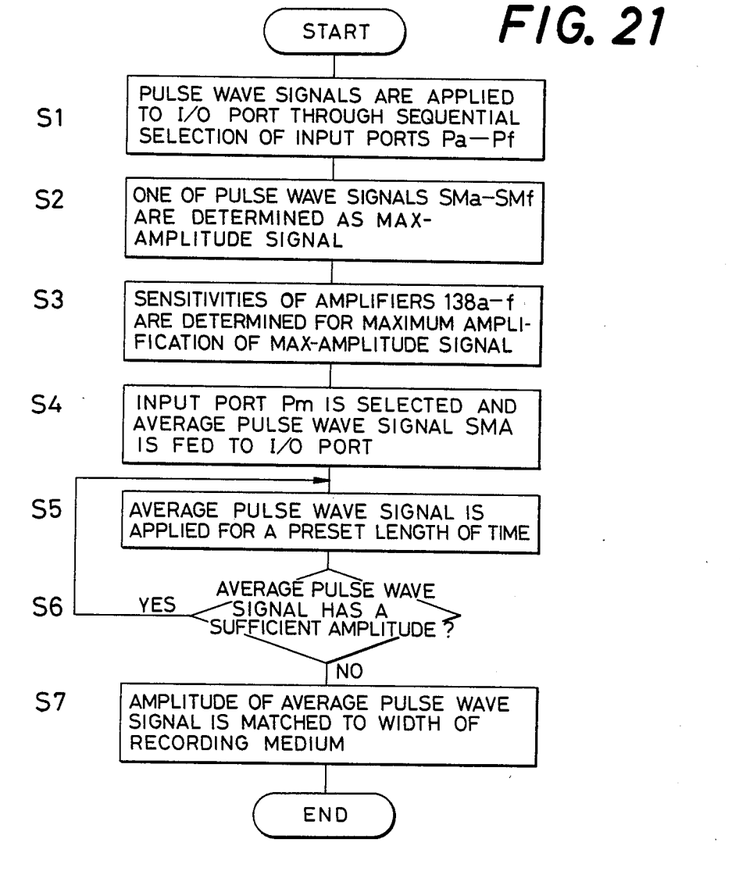
FIG. 21 is a flow chart showing the operation of the apparatus of FIG. 20.
Figure 22:
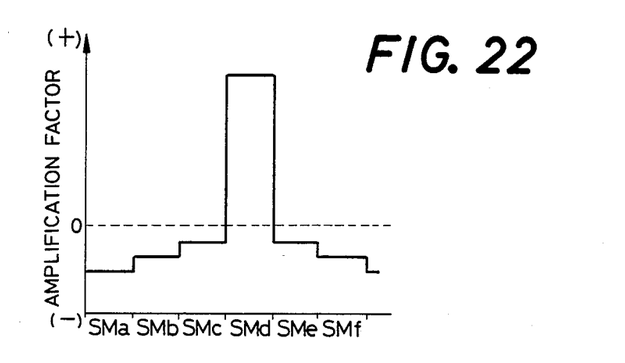
FIG. 22 is a graphical view representing amplification factors applied to the individual pulse wave signals, by a variable amplifier of the control circuit of FIG. 20.

Referring to FIGS. 20–22, there will be described a device for displaying a pulse wave form based on the pulse wave signals produced by the detector of FIGS. 12–18.

There is shown in FIG. 20 a control circuit wherein the pulse wave signals from the individual sensing units 66a through 66f of the sensing device 62 are fed to respective variable-sensitivity amplifiers 138a–138f and an averaging circuit 140 through pre-amplifiers 136a–136f, and also fed to respective input ports Pa-Pf of a multiplexer 142 through bandpass filters 144a–144f.

The variable-sensitivity amplifiers 138a–138f provided as variable amplifier means, amplify the received PULSE WAVE signals SMa-SMf by amplification factors designated by AMPLIFICATION FACTOR signals SSa-SSf from a sensitivity setting interface 146 described later. The amplified PULSE WAVE signals SMa-SMf from the amplifiers 138a–138f are fed to an averaging circuit 148 which is provided as averaging means for averaging the amplified PULSE WAVE signals SMa-SMf and presenting an AVERAGE PULSE WAVE signal SMA to an input port Pm of the multiplexer 142.

The previously indicated averaging circuit 140 which is provided to detect a variation in pressing force applied to the housing 64, averages the received PULSE WAVE signals SMa-SMf and applies the averaged signal to a low pass filter 150. The low pass filter 150 attenuates an oscillating component of the averaged PULSE WAVE signal and transmits to an input port Pd of the multiplexer 142 a DRIFT signal representing only a static drift component of the PULSE WAVE signal.

The multiplexer 142 selects its input ports according to SELECT signals SL supplied from a port-selecting interface 152 described later. The PULSE WAVE signal applied to the selected input port is fed to an oscillograph 154 designed as display means, and to an I/O port 158 through an A/D (analog-digital) converter 156 which is connected to a CPU (central processing unit) 160, a RAM (random-access memory) 162 and a ROM (read-only memory) 164 through a data bus line. The CPU 160 provided as control means, executes signal processing operations based on a program stored in the ROM 164 and by means of utilizing a memory function of the RAM 162. The CPU 160 feeds a SENSITIVITY SELECT signal SO and a PORT SELECT signal SP to the sensitivity-selecting interface 146 and the port-selecting interface 152, respectively, and feeds a DISPLAY signal SH to a printer drive circuit 166. This drive circuit 166 applies a PRINTER DRIVE signal SHD to a printer 168 provided as another display means for indicating a pulse wave form represented by the DISPLAY signal. The printer 168 may be a dot-matrix printer, a pen-type plotter, or other graphically indicating devices.

The I/O port 158 also feeds a PRESSING FORCE DISPLAY signal PP to a pressing-force indicator 170 which provides an analog display of pressing forces of the individual sensing units 66a–66f in the form of bar graphs, whereby the adequacy of the pressing force can be monitored.

Referring to a flow chart of FIG. 21, the operation of the present control system is explained below.

Upon positioning of the sensing device 62 in pressed contact with the neck of a human body so that the sensing units 66a–66f are arranged in a direction across the carotid artery, the individual sensing units 66a–66f generate PULSE WAVE signals magnitudes of which are increased in proportion to the lateral distance of the units to the carotid artery. In other words, the sensing unit 66 which is closest to the carotid artery produces a PULSE WAVE signal of the greatest amplitude. In this condition, a first Step S1 of FIG. 21 is executed, wherein the CPU 160 sends the PORT SELECT signals SP to the port-selecting interface 152 so that the PULSE WAVE signals SMa-SMf are sequentially applied to the I/O port 158 through the input ports Pa-Pf of the multiplexer 142. As a result, the SELECT signals SL are fed from the port-selecting interface 152 to the multiplexer 142 to select the input ports Pa-PF in order, and the PULSE WAVE signals SMa-SMf are applied to the I/O port 158 one after another. Successively, the control goes to a comparing and determining Step S2 wherein the amplitudes of the PULSE WAVE signals SMa-SMf are compared with each other, and one of these signals SMa-SMf is determined to be a maximum-amplitude PULSE WAVE signal. The Step S2 is followed by a Step S3 wherein the sensitivities of the variable-sensitivity amplifiers 138 are determined for amplification of the PULSE WAVE signals SMa-SMf so that the amplification-factor curve is of a mountain-like form with the peak corresponding to the maximum-amplitude PULSE WAVE signal SM. The I/O port 158 feeds to the sensitivity-setting interface 146 the SENSITIVITY SELECT signals SO based on the determined sensitivities, and the sensitivity-setting interface 146 feeds to the variable-sensitivity amplifiers 138a–138f the AMPLIFICATION FACTOR signals SSa-SSf representative of the determined sensitivities. For example, when the PULSE WAVE signal SMd is determined as the maximum-amplitude PULSE WAVE signal, the PULSE WAVE signals SMa-SMf are amplified by amplification factors as shown in FIG. 22, and the amplified signals are applied to the averaging circuit 148. Stated more specifically, the amplification factors for the individual PULSE WAVE signals SMa-SMf are selected such that a positive factor is applied only to the amplifier 138d and different negative factors are applied to the other amplifiers 138a–138c and 138e–138f. Further, the sum of all factors is determined to be zero, and the negative factors are increased toward zero as the applicable PULSE WAVE signals SMa-SMc and SMe-SMf in the abscissa of FIG. 22 come closer to the maximum-amplitude PULSE WAVE signal SMd. In other words, a weighting operation is performed by applying a positive weight to the maximum-amplitude PULSE WAVE signal SMd, and negative weights to the other PULSE WAVE signals SMa-SMc and SMe-SMf, the sum of the positive and negative weights being equal to zero.

Then, the control goes to a Step S4 wherein the input port Pm of the multiplexer 142 is selected, and the AVERAGE PULSE WAVE signal SMA produced by the averaging circuit 148 (by means of averaging the amplified PULSE WAVE signals SMa-SMf) is transmitted to the oscillograph 154 and to the I/O port 158. Since the PULSE WAVE signals SMa-SMf are weighted by the amplifiers 138 and subsequently averaged by the averaging circuit 148, as discussed above, noises which were equally included in the signals SMa-SMf are effectively removed from the AVERAGE PULSE WAVE signal SMA. Accordingly, a pulse waveform as shown in FIG. 4 for example, is displayed on the oscillograph 154 in a real time fashion even if noises are produced due to simultaneous changes in depression pressure of the sensing units 66a–66f, caused by a quick movement of the neck of the subject or by a variation in pressing force being applied to the housing 64 of the sensing device 62.

Subsequently, the control goes to a Step S5 wherein the AVERAGE PULSE WAVE signal SMA is kept applied to the input port Pm for a preset length of time, e.g., 10 seconds. In the next Step S6, the applied signal SMA is monitored to check if its amplitude is not less than a predetermined lower limit. In the event the amplitude of the AVERAGE PULSE WAVE signal SMA is lower than the predetermined limit, the control returns to the preceding Step S5. If the amplitude is higher than the limit, the Step S6 is followed by a Step S7 wherein the amplitude of the AVERAGE PULSE WAVE signal SMA is matched to a width of a recording medium (sheet of paper) and the pulse waveform corresponding to the signal SMA is indicated on the recording medium on the printer 168. Described more particularly, the AVERAGE PULSE WAVE signal SMA is modified so that the maximum amplitude of the signal SMA is equal to a preset percent, e.g., 80%, of the overall width of the recording paper, and the DISPLAY signal SH corresponding to the modified signal SMA is supplied to the printer drive circuit 166 which in turn feeds the PRINTER DRIVE signal SHD to the printer 168, whereby a pulse waveform similar to that displayed on the oscillograph 154 is recorded in an easy-to-watch area of the recording paper on the printer 168.

The drift component of the PULSE WAVE signals SMa-SMf averaged by the averaging circuit 140 and filtered by the low pass filter 150 is monitored to check, according to a flow chart (not shown), whether or not the depression pressure is in the specified optimal range. At the same time, the depression pressure is indicated on the indicator 170 which is provided with means for indicating the optimal range of the depression pressure.

As discussed hitherto, the PULSE WAVE signals SM generated by the plural sensing units 66 are weighted and averaged to remove the noises which are equally included in the individual signals SM when the sensing device 62 is subject to a quick movement of the subject or when the force applied to the housing 64 is abruptly changed. Thus, the present embodiment of the detecting apparatus is capable of providing a precise display of a pulse waveform of an arterial vessel, particularly of the carotid artery.

The precision of the pulse waveform is further attributed to the previously indicated manner of determination of the negative weights which are applied in the Step S3. That is, the negative weights to be applied to the PULSE WAVE signals except the maximum-amplitude PULSE WAVE signal are determined such that the closer the applicable sensing units to the sensing unit generating the maximum-amplitude PULSE WAVE signal, the smaller minus weights are used. This means that the pulse wave signals generated by the sensing units closer to the carotid artery have less distortion and are consequently more desired to be used as a source of substantive weight upon which the pulse waveform of the carotid artery is displayed.

While the detecting apparatus including the sensing device 62 has been described in association with the control system specifically illustrated in FIGS. 20-22, the apparatus may be embodied in other forms.

For example, the preceding embodiment uses the oscillograph 154 for real-time display of the pulse waveform of the carotid artery, as well as the printer 168 which effects a printing of the pulse waveform based on the AVERAGE PULSE WAVE signal SMA which has been checked for its sufficient amplitude. However, the apparatus need not be provided with both the oscillograph 154 and the printer 168; the apparatus may function satisfactorily when either one of the oscillograph and the printer is provided.

Further, it is possible to apply the same negative weights to the PULSE WAVE signals except the maximum-amplitude signal.

Although the foregoing control system is used in connection with the sensing device 62 equipped with the sensing unit 66a–66f, the attenuation or elimination of noises can be achieved even when the control system is used for the detector 22 of FIGS. 6-8 or for a traditional detector wherein sensing units are directly fixed to a housing.

If desired, the pressing force indicator 170 may be provided on the housing 64. This arrangement is advantageous in that the operator or user can easily know, during depression of the sensing device 62 onto the neck, wether the neck is depressed with a suitable force or not.

While the present invention has been described in its preferred embodiments, it is to be understood that the invention is not limited thereto and that various changes and modifications may be made without departing from the scope of the invention defined by the appended claims.

What is claimed is:

1. A pulse wave detecting apparatus including a detector adapted to be depressed at its depression surface onto a body member of a subject to detect a blood pressure pulse wave of an artery, said detector comprising:
  a housing having portions defining an air chamber which is open at one end thereof, the open end of said housing defining a plane of said depression surface;
  a sensing unit received in said air chamber movably in a first direction parallel to a direction in which said detector is depressed onto said body member, said sensing unit including a presser portion protruding away from said depression surface, an elastic member elastically deformable in response to a movement of said presser portion in said first direction, a strain gauge held in contact with said elastic member for generating a pulse wave signal corresponding to an amount of elastic deformation of said elastic member and representing the pulse wave of said artery transmitted through said presser portion, and a support structure partially received in said air chamber of said housing and movable in said first direction, said support structure supporting said elastic member so as to permit elastic deformation thereof; and
  elastic support means provided in said housing for resiliently supporting said support structure of said sensing unit depression of said detector onto said body member establishing a depression pressure between said presser portion and said body member in a specified optimal range.

2. A detecting apparatus as recited in claim 1, wherein said sensing unit further comprises:
  a resilient diaphragm secured at its periphery to said housing so as to cover said air chamber at said one end thereof and to form said depression surface, and having a central movable portion on which said presser portion is integrally formed;
  said elastic member being deformable in contact with an inner surface of said central portion of said resilient diaphragm upon movements of said central portion.

3. A detecting apparatus as recited in claim 1, wherein said support structure comprises
  a movable housing, and said sensing unit further comprises a presser member provided movably in said first direction relative to said movable housing, said presser member having said presser portion and being biased in a direction that causes said presser portion to protrude from said plane of the depression surface;
  said elastic member being elastically deformable in response to relative movement between said presser member and said movable housing.

4. A detecting apparatus as recited in claim 1, wherein said elastic support means comprises a layer of spongy material interposed compressibly between said sensing unit and a bottom of said housing at the other end thereof opposite to said depression surface.

5. A detecting apparatus as recited in claim 1, wherein said elastic support means comprises a compression coil spring interposed between said sensing unit and a bottom of said housing at the other end thereof opposite to said depression surface.

6. A detecting apparatus as recited in claim 3, wherein said elastic member comprises a metal sheet including a relatively rigid sensed portion an elastic deformation of which is detected by said strain gauge, and an operated portion which is integrally united with said sensed portion and more easily deformable, than said sensed portion, in response to said relative movement, said strain gauge comprising a semi-conductor strain gauge adhering to said sensed portion.

7. A carotid artery pulse wave detecting apparatus, including a detector adapted to be depressed at its depression surface onto the neck of a subject to detect a blood pressure pulse wave of the carotid artery, said detector comprising:
  a housing having portions defining an air chamber which is open at one end thereof, the open end of said housing defining a plane of said depression surface; and
  a plurality of sensing units each received in said air chamber movably in a first direction parallel to a direction in which the detector is depressed onto the neck, each of said sensing units including a presser portion protruding away from said depression surface, said each sensing unit detecting the pulse wave of said carotid artery transmitted through said presser portion, and generating a pulse wave signal, the presser portions of said sensing units being disposed such that a plurality thereof are disposed along a line intersecting the carotid artery and spaced from each other by a distance of not more than 15 mm in a second direction perpendicular to said carotid artery, when the detector is depressed onto the neck of the subject.

8. A detecting apparatus as recited in claim 7, wherein said detector further comprises elastic support means provided in said housing for resiliently supporting each of said plurality of sensing units, upon depression of the detector onto the neck, with an elastic force thereof so as to establish a depression pressure between said presser portion and the neck in a specified optimal range.

9. A detecting apparatus as recited in claim 8, wherein said each sensing unit comprises:
 a resilient diaphragm secured at its periphery to said housing so as to cover said air chamber at said one end thereof and to form said depression surface, and having a central movable portion on which said presser portion is integrally formed;
 an elastic member received in said air chamber of said housing, and elastically deformable in direct or indirect contact with an inner surface of said central portion of said resilient diaphragm upon movements of said central portion;
 a strain gauge held in contact relation with said elastic member and generating said pulse wave signal corresponding to an elastic deformation of said elastic member; and
 a support structure received in said housing movably in said first direction and supporting said elastic member to permit said elastic deformation thereof,
 and, wherein said elastic support means comprises a layer of spongy material interposed compressibly between said support structure and a bottom of said housing at the other end thereof opposite to said depression surface.

10. A detecting apparatus as recited in claim 9, wherein the resilient diaphragms of the individual sensing units are formed on a single common resilient diaphragm on which the presser members of the respective sensing units are integrally secured.

11. A detecting apparatus as recited in claim 8, wherein said each sensing unit comprises:
 a movable housing at least partially received in said air chamber of said housing movably in said first direction;
 a presser member provided movably in said first direction relative to said movable housing, said presser member having said presser portion and being biased in a direction that causes said presser portion to protrude from said plane of the depression surface;
 an elastic member received in said housing and elastically deformable in response to a relative movement between said presser member and said movable housing; and
 a strain gauge held in contact relation with said elastic member and generating said pulse wave signal corresponding to an elastic deformation of said elastic member,
 and, wherein said elastic support means comprises a compression coil spring interposed between said each sensing unit and a bottom of said housing at the other end thereof opposite to said depression surface.

12. A pulse wave detecting apparatus, including a detector adapted to be depressed at its depression surface onto a body member of a subject to detect a blood pressure pulse wave of an artery, said detector comprising:
 a sensing device depressed onto the body member and detecting the pulse wave of said artery to generate a pulse wave signal; and
 holder means having at one end thereof a universal joint for pivotably connecting said sensing device to said holder means, said holder means gripping, with a predetermined pressure of depression, the body member of the subject between the other end thereof and said sensing device, thereby holding said sensing device in contact with said body member of the subject at a predetermined portion of the latter with a predetermined force of depression.

13. A detecting apparatus as recited in claim 12, wherein said holder means comprises a presser pad provided at said other end thereof, said body member of the subject being gripped between said presser pad and said sensing device.

14. A detecting apparatus as recited in claim 12, wherein said holder means comprises a first arm connected at one end to said sensing device, and a second arm pivotably connected at one end thereof to the other end of said first arm, said holder means further comprising tensioning means associated with said first and second arms to bias the same toward each other.

15. A detecting apparatus as recited in claim 12, wherein said sensing device comprises:
 a housing having portions defining an air chamber which is open at one end thereof, the open of said housing defining a plane of said depression surface;
 a sensing unit received in said air chamber movably in a first direction parallel to a direction in which the sensing device is depressed onto the body member, said sensing unit including a presser portion protruding away from said depression surface, said sensing unit detecting the pulse wave of said artery transmitted through said presser portion, and generating a pulse wave signal; and
 elastic support means provided in said housing for resiliently supporting said sensing unit, upon depression of the detector onto the body member, with an elastic force thereof so as to establish a depression pressure between said presser portion and the body member in a specified optimal range.

16. A detecting apparatus as recited in claim 15, wherein said sensing unit comprises:
 a resilient diaphragm secured at its periphery to said housing so as to cover said air chamber at said one end thereof and to form said depression surface, and having a central movable portion on which said presser portion is integrally formed;
 an elastic member received in said air chamber of said housing, and elastically deformable in direct or indirect contact with an inner surface of said central portion of said resilient diaphragm upon movements of said central portion;
 a strain gauge held in contacting relation with said elastic member and generating said pulse wave signal corresponding to an elastic deformation of said elastic member; and
 a support structure received in said housing movably in said first direction and supporting said elastic member to permit said elastic deformation thereof, said support structure being supported by said elastic support means.

17. A detecting apparatus as recited in claim 15, wherein said sensing unit comprises:
   a movable housing at least partially received in said air chamber of said housing movably in said first direction;
   a presser member provided movably in said first direction relative to said movable housing, said presser member having said presser portion and being biased in a direction that causes said presser portion to protrude from said plane of the depression surface;
   an elastic member received in said housing and elastically deformable in response to a relative movement between said presser member and said movable housing; and
   a strain gauge held in contacting relation with said elastic member and generating said pulse wave signal corresponding to an elastic deformation of said elastic member.

18. A detecting apparatus as recited in claim 12, wherein said sensing device comprises:
   a housing having portions defining an air chamber which is open at one end thereof, the open end of said housing defining a plane of said depression surface; and
   a plurality of sensing units each received in said air chamber movably in a first direction parallel to a direction in which the sensing device is depressed onto the body member, each of said sensing units including a presser portion protruding away from said depression surface, said each sensing unit detecting the pulse wave of said artery transmitted through said presser portion, and generating a pulse wave signal, the presser portions of said sensing units being disposed such that a plurality thereof are disposed along a line intersecting the artery and spaced from each other by a distance of not more than 15 mm in a second direction perpendicular to said artery, when the detector is depressed onto the body member of the subject.

19. A detecting apparatus as recited in claim 18, wherein said sensing device further comprises elastic support means provided in said housing for resiliently supporting each of said plurality of sensing units, upon depression of the sensing device onto the body member, with an elastic force thereof so as to establish a depression pressure between said presser portion and the body member in a specified optimal range.

20. A detecting apparatus as recited in claim 19, wherein said each sensing unit comprises:
   a resilient diaphragm secured at its periphery to said housing so as to cover said air chamber at said one end thereof and to form said depression surface, and having a central movable portion on which said presser portion is integrally formed;
   an elastic member received in said air chamber of said housing, and elastically deformable in direct or indirect contact with an inner surface of said central portion of said resilient diaphragm upon movements of said central portion;
   a strain gauge held in contacting relation with said elastic member and generating said pulse wave signal corresponding to an elastic deformation of said elastic member; and
   a support structure received in said housing movably in said first direction and supporting said elastic member to permit said elastic deformation thereof,
   and, wherein said elastic support means comprises a layer of spongy material interposed compressibly between said support structure and a bottom of d housing at the other end opposite to said depression surface.

21. A detecting apparatus as recited in claim 19, wherein said each sensing unit comprises:
   a movable housing at least partially received in said air chamber of said housing movably in said first direction;
   a presser member provided movably in said first direction relative to said movable housing, said presser member having said presser portion and being biased in a direction that causes said presser portion to protrude from said plane of the depression surface;
   an elastic member received in said housing and elastically deformable in response to a relative movement between said presser member and said movable housing; and
   a strain gauge held in contacting relation with said elastic member and generating said pulse wave signal corresponding to an elastic deformation of said elastic member,
   and, wherein said elastic support means comprises a compression coil spring interposed between said each sensing unit and a bottom of aid housing at the other end thereof opposite to said depression surface.

22. A method of detecting blood pressure pulsations of an artery of a subject and displaying a pulse wave form thereof, based on pulse wave signals generated from a plurality of sensing units disposed in a housing of a detector which is adapted to be depressed at its depression surface onto the body member of said subject, said method comprising the steps of:
   comparing amplitudes of said pulse wave signals with each other, and determining one of said pulse wave signals to be a maximum-amplitude pulse wave signal;
   weighting said pulse wave signals by applying a positive weight to said maximum-amplitude pulse wave signal and negative weights to the other pulse wave signals, a sum of said positive weight and said negative weights being zero;
   averaging the weighted pulse signals to produce an averge pulse wave signal; and
   displaying said pulse wave form of said artery in response to said average pulse wave signal.

23. A pulse wave detecting apparatus, comprising:
   a detector including a housing and a plurality of sensing units which are received in said housing and adapted to be depressed at the depression surface onto a body member of a subject to detect a blood pressure pulse wave of an artery, said sensing units generating pulse wave signals representing pulsations of the artery;
   variable amplifier means, connected to said sensing units, for amplifying said pulse wave signals from the respective sensing units;
   averaging means for averaging said pulse wave signals amplified by said variable amplifier means, and producing an average pulse wave signal;

display means for displaying a pulse wave form representing the pulsations of the arteary, based on said average pulse wave signal; and control means including means for determining one of said pulse wave signals from said sensing units to be a maximum-amplitude pulse wave signal, said control means directing said variable amplifier means to amplify said maximum-amplitude pulse wave signal by a positive amplification factor and the other pulse wave signals by negative amplification factors, a sum of said positive amplification factor and said negative amplification factors being zero.

24. A detecting apparatus as recited in claim 23, wherein said detector further comprises elastic support means provided in said housing and said housing has portions defining an air chamber which is open at one end thereof, the open end of said housing defining a plane of said depression surface, each of said plurality of sensing units being received in said air chamber movably in a first direction parallel to a direction in which the detector is depressed onto the body member, said each sensing unit including a presser portion protruding away from said depression surface, said sensing unit detecting the pulse wave transmitted through said presser portion, and generating a pulse wave signal, said elastic support means resiliently supporting said each sensing unit, upon depression of the detector onto the body member, with an elastic force thereof so as to establish a depression pressure between said presser portion and the body member in a specified optimal range.

25. A detecting apparatus as recited in claim 23, wherein each of said plurality of sensing units includes a presser portion protruding away from said depression surface, the presser portions of said sensing units being disposed such that a plurality thereof are spaced from each other by a distance of not more than 15 mm in a second direction perpendicular to said artery when the detector is depressed onto the body member of the subject.

26. A detecting apparatus as recited in claim 23, wherein said detector comprises a sensing device constituted by said plurality of sensing units, and further comprises holder means carrying at one end thereof said sensing device, said holder gripping, with a predetermined pressure of depression, the body member of the subject between the other end thereof and said sensing device, thereby holding said sensing device in contact with said body member of the subject at a predetermined portion of the latter with a predetermined force of depression.

* * * * *